(12) United States Patent
Hurvitz et al.

(10) Patent No.: US 7,986,404 B2
(45) Date of Patent: Jul. 26, 2011

(54) INSPECTION SYSTEM EMPLOYING ILLUMINATION THAT IS SELECTABLE OVER A CONTINUOUS RANGE ANGLES

(75) Inventors: Tali Hurvitz, Ramat Hasharon (IL); Yariv Dror Mizrahi, Ranana (IL); David Fisch, Paduelle (IL)

(73) Assignee: Orbotech Ltd., Yavne (IL)

( * ) Notice: Subject to any disclaimer, the term of this patent is extended or adjusted under 35 U.S.C. 154(b) by 345 days.

(21) Appl. No.: 12/295,514

(22) PCT Filed: Mar. 20, 2007

(86) PCT No.: PCT/IB2007/002845
§ 371 (c)(1),
(2), (4) Date: Oct. 29, 2008

(87) PCT Pub. No.: WO2007/144777
PCT Pub. Date: Dec. 21, 2007

(65) Prior Publication Data
US 2010/0231901 A1    Sep. 16, 2010

Related U.S. Application Data

(60) Provisional application No. 60/787,230, filed on Mar. 30, 2006.

(51) Int. Cl.
*G01N 21/00* (2006.01)
(52) U.S. Cl. .................. 356/237.2; 356/237.1
(58) Field of Classification Search ..... 356/237.1–237.5
See application file for complete search history.

(56) References Cited

U.S. PATENT DOCUMENTS

| | | | |
|---|---|---|---|
| 4,660,980 A | 4/1987 | Takabayashi et al. |
| 4,693,601 A | 9/1987 | Dabelstein et al. |
| 4,707,611 A | 11/1987 | Southwell |
| 4,893,024 A | 1/1990 | Koashi et al. |
| 4,899,055 A | 2/1990 | Adams |
| 4,914,309 A | 4/1990 | Masaharu et al. |
| 4,999,014 A | 3/1991 | Gold et al. |
| 5,034,617 A | 7/1991 | Isobe |
| 5,164,603 A | 11/1992 | Hartman et al. |
| 5,235,547 A | 8/1993 | Kobayashi |
| 5,293,214 A | 3/1994 | Ledger |
| 5,333,049 A | 7/1994 | Ledger |

(Continued)

FOREIGN PATENT DOCUMENTS

JP   2006226804   8/2006

(Continued)

*Primary Examiner* — Michael P. Stafira
(74) *Attorney, Agent, or Firm* — Sughrue Mion, PLLC

(57) ABSTRACT

An illumination device and method for inspecting objects having microscopic features is provided. The device includes an illuminator which provides a solid angle of angularly specific illumination defining an illumination angle, selected by a user from among a continuous range of possible illumination angles. The device further includes an object inspector which inspects the object illuminated by the illuminator. The illuminator may include an illumination source, a light concentrator, an illumination angle selector, disposed along a light path between the illumination source and the object inspector. The illumination angle selector may have a first position in which directly-reflected light propagates toward the object plane and a second position in which no light both selected by the illumination angle selector and directly reflected from the object plane enters the collecting lens. Rather, in the second position, only scattered light from the object plane enters the collecting lens.

15 Claims, 3 Drawing Sheets

Dark Field Illumination with shifted mirror another state

U.S. PATENT DOCUMENTS

| | | | |
|---|---|---|---|
| 5,337,150 | A | 8/1994 | Mumola |
| 5,729,343 | A | 3/1998 | Aiyer |
| 5,838,448 | A | 11/1998 | Aiyer et al. |
| 5,900,939 | A | 5/1999 | Aspnes et al. |
| 5,963,254 | A | 10/1999 | Kim et al. |
| 6,538,730 | B2 | 3/2003 | Vaez-Iravani et al. |
| 6,654,129 | B1 | 11/2003 | Uda et al. |
| 6,731,380 | B2 | 5/2004 | Amara et al. |
| 6,781,103 | B1 | 8/2004 | Lane et al. |
| 6,847,442 | B1 * | 1/2005 | Katzir et al. ............... 356/237.2 |
| 6,975,410 | B1 | 12/2005 | Sturgill |
| 6,982,796 | B2 | 1/2006 | Sato |
| 6,999,180 | B1 | 2/2006 | Janik et al. |
| 7,001,055 | B1 | 2/2006 | Lange |
| 7,030,998 | B2 | 4/2006 | Takeuchi et al. |
| 7,139,081 | B2 | 11/2006 | De Groot |
| 7,161,668 | B2 | 1/2007 | Meeks et al. |
| 7,177,030 | B2 | 2/2007 | Leizerson et al. |
| 7,215,417 | B2 * | 5/2007 | Katzir et al. ............... 356/237.2 |
| 7,230,243 | B2 | 6/2007 | Tanaka et al. |
| 2002/0145732 | A1 | 10/2002 | Vaez-Iravani et al. |
| 2003/0094586 | A1 | 5/2003 | Kurosawa et al. |
| 2005/0168729 | A1 | 8/2005 | Jung et al. |
| 2005/0179910 | A1 | 8/2005 | Bartov |
| 2006/0012778 | A1 | 1/2006 | Vaughnn |
| 2007/0058164 | A1 | 3/2007 | Shibata et al. |
| 2007/0081167 | A1 | 4/2007 | De Groot |
| 2007/0115461 | A1 | 5/2007 | Fairley et al. |
| 2007/0121106 | A1 | 5/2007 | Shibata et al. |

FOREIGN PATENT DOCUMENTS

| | | |
|---|---|---|
| JP | 2006292668 | 10/2006 |

* cited by examiner

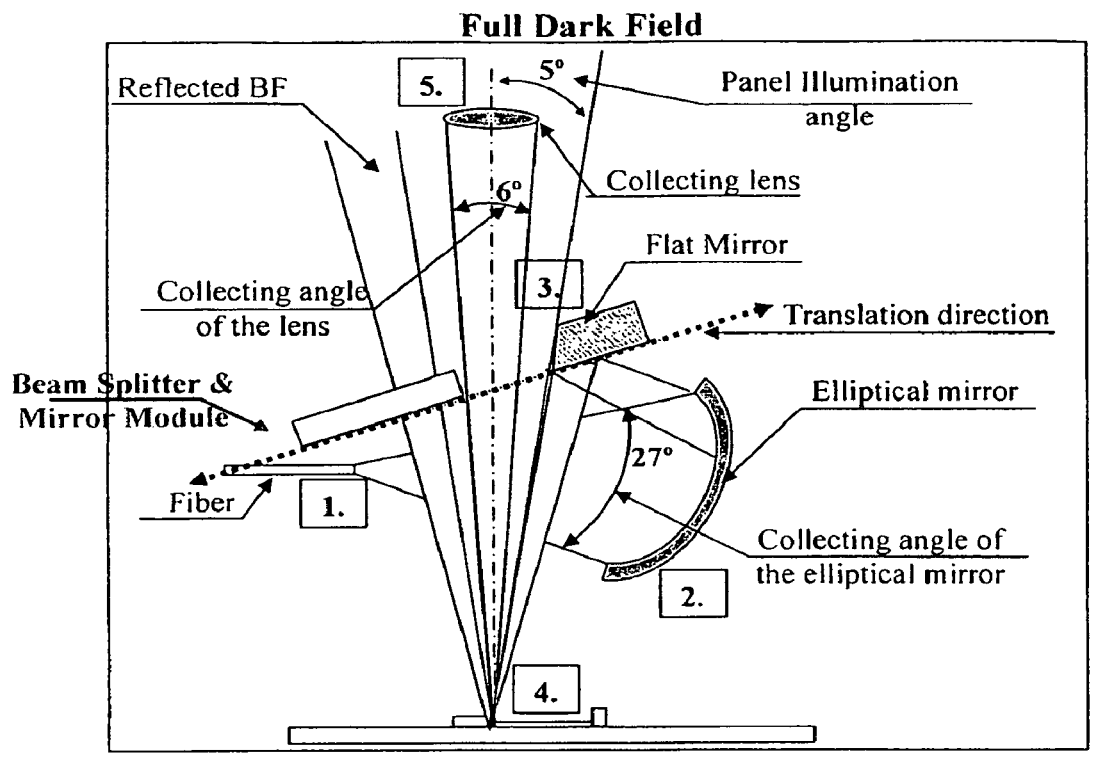
Figure 1: Dark Field Illumination with shifted mirror another state
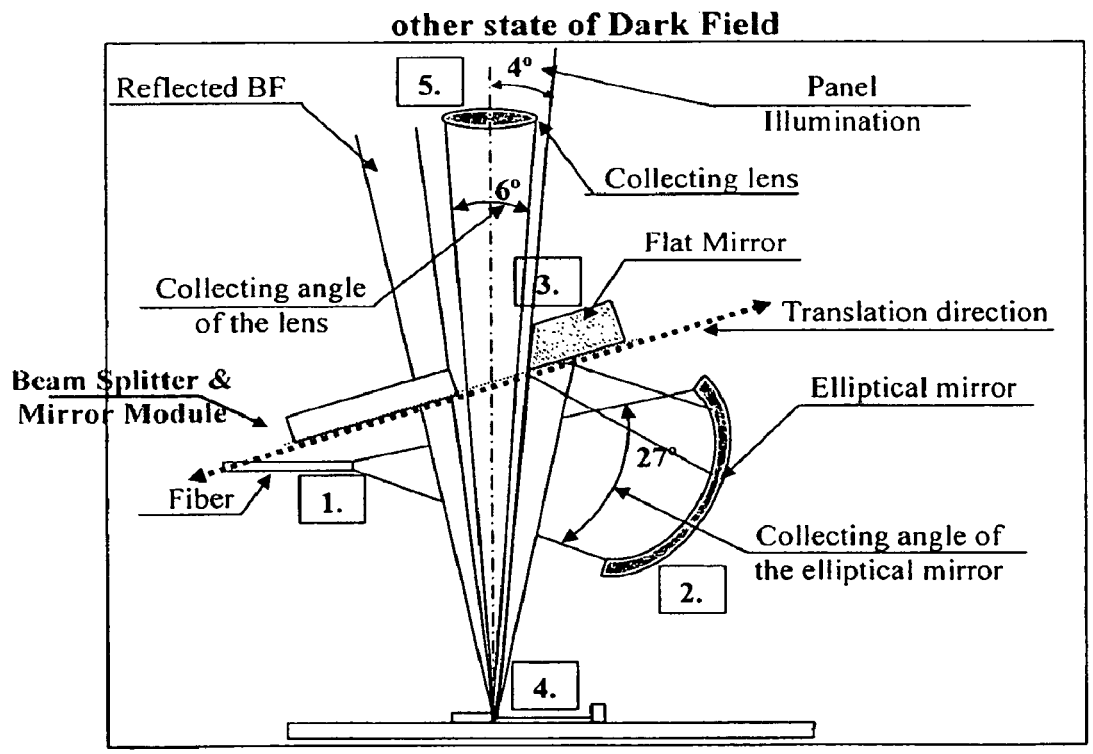
Figure 2: Dark Field Illumination with shifted mirror – another state

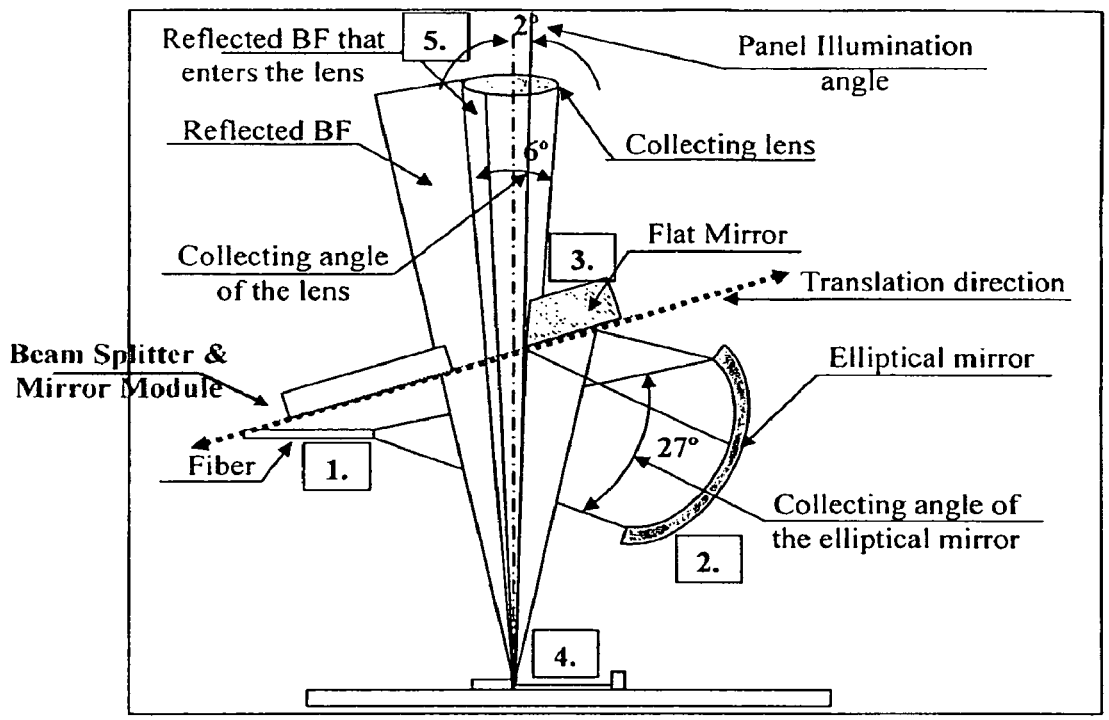
Figure 3: Semi-Dark Field Illumination with shifted mirror – Other state
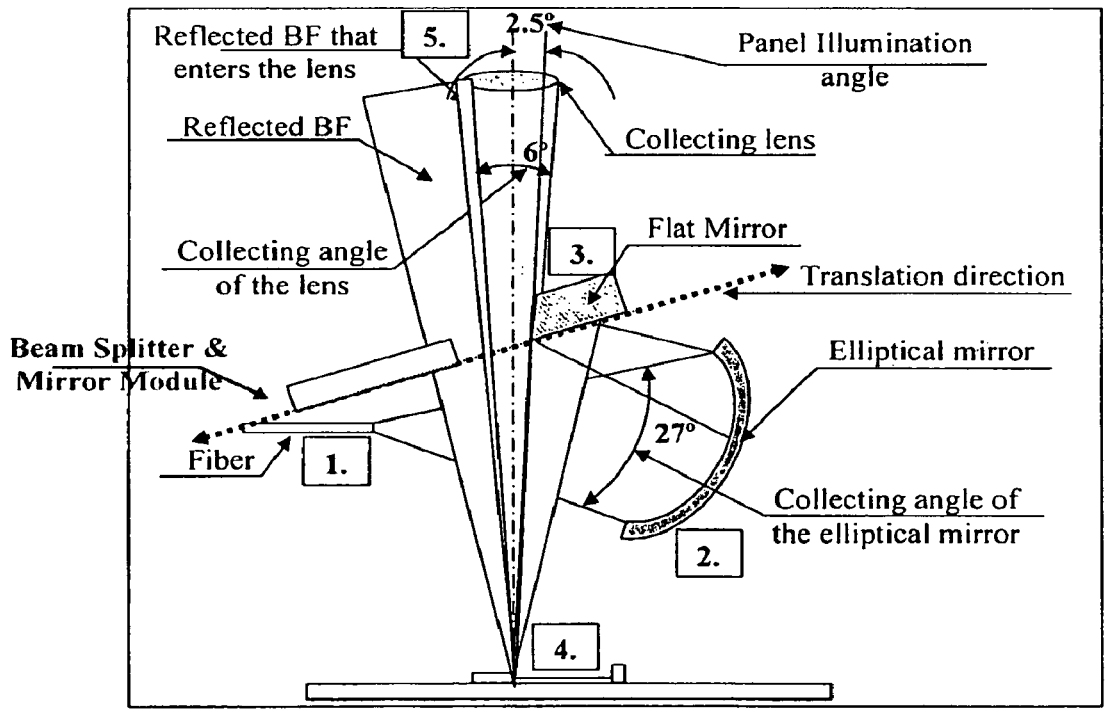
Figure 4 : Semi-Dark Field Illumination with shifted mirror - other state

US 7,986,404 B2

INSPECTION SYSTEM EMPLOYING ILLUMINATION THAT IS SELECTABLE OVER A CONTINUOUS RANGE ANGLES

CROSS-REFERENCE TO RELATED PATENT APPLICATIONS

This Application claims the benefit of U.S. Provisional Application No. 60/787,230, filed on Mar. 30, 2006, the entire disclosure of which is incorporated herein by reference.

BACKGROUND OF THE INVENTION

1. Field of the Invention

Methods and apparatuses consistent with the present invention are related to inspection system for inspection of flat panel displays.

2. Description of the Related Art

Conventional inspection systems for flat panel displays use bright field reflective illumination for image acquisition. Defect detection relies on contrast between materials on the panel, inter alia. However, some of the panel materials are designed to be transparent, for example ITO (indium tin oxide), and creating suitable contrast between these materials and other materials on a panel can be very difficult.

SUMMARY OF THE INVENTION

In accordance with an embodiment of the invention the ability to enhance contrast in the image uses a controlled illumination angle. A substrate to be imaged is selectably illuminated using various combinations of illumination having a controlled angle, including bright field, semi-dark field, dark field or deep dark field. Since the contrast of the image of the substrate depends on the specific pattern, and/or the composition of materials, controlling the angle of illumination enables the system to reach a "best" or good contrast for each inspected pattern.

In accordance with another embodiment of the invention is the ability to add the above features and still retain conventional bright field illumination ability on the same apparatus.

The device shown and described herein is particularly suitable for applications in which transparent layers are to be inspected. Such improved detection performance may be greatly appreciated by custom realization of a solution using the widely collected angles of an elliptical mirror.

Several illumination modes may be provided, including some or all of the following types of illumination: Bright Field (BF), Dark Field (DF), and Semi Dark Field (SDF).

There is thus provided, in accordance with an exemplary embodiment of the present invention, an inspection system for inspecting objects with microscopic features, the inspection system comprising an illuminator operative to provide illumination of an object having microscopic features, the illumination providable over a continuous range of selectable illumination angles, an object inspector inspecting the object with microscopic features under said illumination; and a dual mode controller operative to control the object inspector to operate in at least two modes including:

a first, learning, mode in which a suitable illumination angle from within said continuous range is identified for an individual set of objects having microscopic features by comparing contrast for at least some of the objects in said set when under each of a plurality of illumination angles; and a second, inspection, mode in which said individual set of objects is inspected under said suitable illumination angle.

Both the first, learning, mode and the second, inspection, mode may be performed in sequence by a single mechanism by imaging and measuring the contrast.

Further, in accordance with an exemplary embodiment of the present invention, the object inspector comprises a collecting lens and the object defines an object plane, and the illuminator comprises: an illumination source; an elliptical mirror facing the illumination source; a flat mirror which faces incoming light from the elliptical mirror, wherein the flat mirror, in at least a first position, reflects light toward the object plane; and a flat mirror relative motion provider operative to provide relative motion of the flat mirror relative to the illumination source and to the elliptical mirror, such that in at least a second position of the flat mirror, no light being reflected from both the mirror and directly reflected by the object enters the collecting lens. In other words, in this second position, light entering the collecting lens has been incident on the object from the elliptical mirror and then has been scattered by the object.

One advantage of an embodiment of the invention, but not necessarily the only advantage, is that individual batches of microscopically featured objects with different contrast characteristics, or even individual areas, each having their own contrast characteristics, within objects belonging to a single batch, can be imaged using an illumination angle which best enhances the particular contrast pattern. Typically, the illumination angle is set once for each recipe, each recipe typically comprising a batch of objects. However, in applications in which glasses with more than one type of display are being inspected, it may be desired to scan using different setups within a single recipe or glass. Also, it may be desired to scan different areas within a single display, such as a "cell area" as opposed to a "connectors area" using different setups.

BRIEF DESCRIPTION OF THE DRAWINGS

FIG. 1 is a simplified optical diagram of apparatus for providing smooth variation of the illumination angle in an inspection system for microscopic objects such as in-fabrication flat panel displays, wherein the apparatus is in a first state for providing dark field illumination;

FIG. 2 is a simplified optical diagram of the apparatus of FIG. 1 in a second state for providing dark field illumination;

FIG. 3 is a simplified optical diagram of the apparatus of FIG. 1 in a third state for providing semi-dark field illumination;

FIG. 4 is a simplified optical diagram of the apparatus of FIG. 1 in a fourth state for providing semi-dark field illumination;

DETAILED DESCRIPTION OF EXEMPLARY EMBODIMENTS OF THE INVENTION

Figure 5:
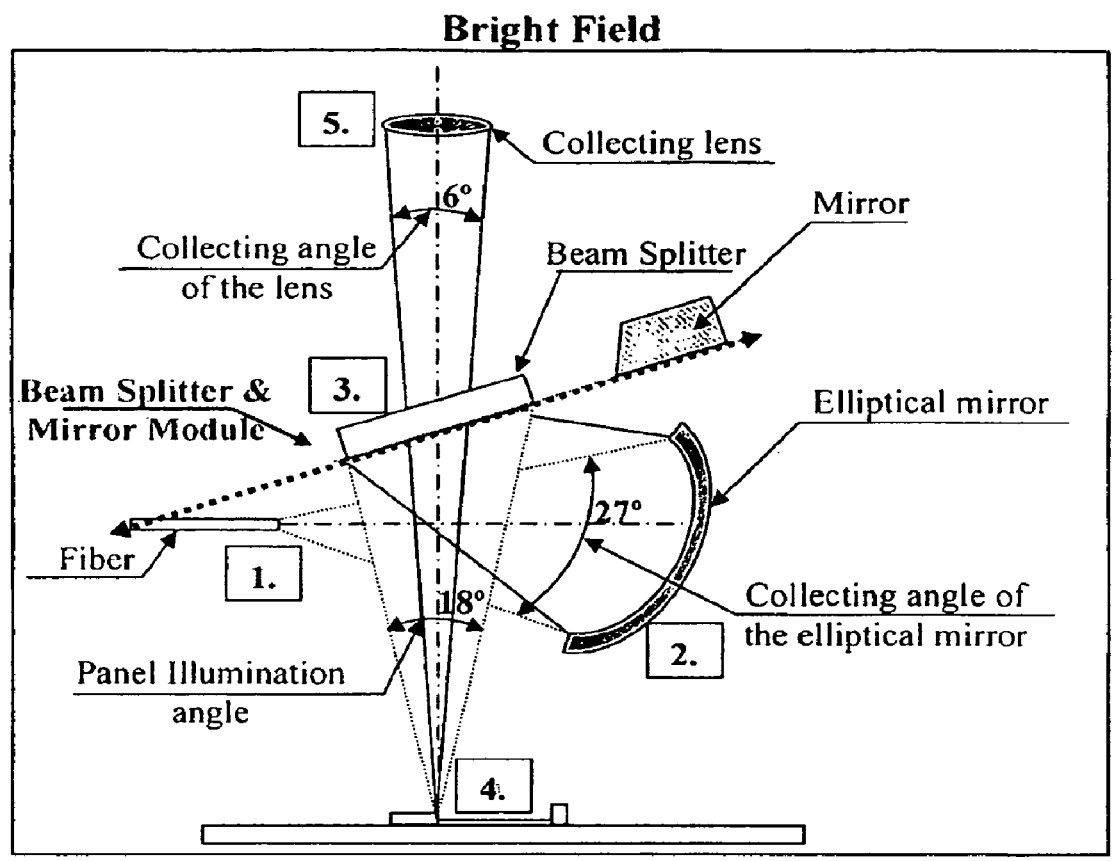
FIG. 5 is a simplified optical diagram of the apparatus of FIG. 1 in a fifth state for providing bright field illumination.

An embodiment of the present invention is shown in FIGS. 1-5 in various states. As shown in FIG. 5, which represents a bright field illumination providing state, an optical beam output from an optical fiber bundle propagates in free space. Suitably the fiber bundle has a numerical aperture of 0.6 (angle)+/−36°, although other suitable illumination sources having other numerical apertures may be employed. A propagating beam reflects from a suitable optical element e.g. an elliptical mirror with a suitable magnification factor such as 1.46. A slider, or beam splitter mirror module, bearing a partially reflecting mirror/beam splitter and a fully reflecting mirror, both of which may be constructed and operative to be translated together is provided. As shown in FIGS. 1-5, an elliptical mirror may collect light from the fiber bundle over an angle of about 27°. The remaining light from the fiber bundle may be treated as stray light. It can be insured that the stray light does not interfere with the illumination or imaging systems by use of appropriate baffles, as would be understood by one of skill in the art.

The beam splitter is arranged to reflect some of the light impinging thereon, e.g. 40% of the light, towards the panel plane. It is noted that the panel plane is the same as the object plane, as discussed above. The may be focused on the panel over a region for which the total angular coverage is e.g. 18°. A collecting lens is positioned along a central optical axis of the system above the panel plane. Typically the collecting lens collects light over a collection angle, e.g. ±3° or 6° total, for example, collects the light reflected from the panel that passes through the Beam Splitter, e.g. with 40% efficiency, and images the light onto the imaging plane of a camera(not shown). The camera provides images to an image processor, which suitably is operative to analyze the images and detect defects in the object that is imaged.

FIGS. 1 and 2 shows an exemplary apparatus, also seen in the other figures, configured in full dark field illumination providing states, each of which is characterized by a different illumination angle. It is appreciated that a continuum of selectable states of illumination, i.e. between angles of dark field illumination, full field/bright field illumination and various states combining both dark field and full field/bright field illumination, is provided by an apparatus of the present invention.

The optical beam output from the fiber bundle has a suitable numerical aperture, e.g. 0.6 (angle is +/−)36°, although light sources having a different NA may also be suitable. The propagating beam reflects from an elliptical mirror with a suitable magnification factor of, for example, 1.46.

The Beam Splitter-Minor Module is set with the Flat Mirror facing the incoming light from the elliptical mirror, the module being arranged to reflect light from the flat mirror towards the panel plane. The slider/beam splitter minor module is shifted relative to the optical axis to provide a selected angle of illumination. For full Dark Field illumination the flat mirror is shifted such that the angle of the light directed onto the panel, e.g. by the flat mirror as seen in the figures, is subsequently reflected by the panel at an angle that misses the objective lens of a viewing camera. The extent of the shift is defined by the application-appropriate dark field angle.

Thus, based on the positioning of the beam splitter and mirror module, a panel in the object plane may be illuminated with light of varying angles, all from a single illuminator: e.g. the fiber bundle, as discussed above. The angle of the light incident on the panel defines the angle at which light is reflected from the panel towards the collecting lens, and the position of the beam splitter and mirror module further determines, as shown in FIGS. 1-5, the angle of light reflected from the panel which is "visible" to the connecting lens. Alternately, the illuminator may comprise a set of individually-controlled illumination devices, such as lamps or diodes.

Light is concentrated onto the panel, typically along a linear scan line, and then reflected from it. In this context, reflection from the panel includes specular reflection as well as diffusive reflection and scattering. An objective lens placed along the central optical axis (typically above the panel plane) is associated with a camera to view the panel. It is noted that the objective lens is the same as the collecting lens, as discussed above. As shown, the angle at which illumination is reflected from the panel in the configuration shown in FIG. 1 is offset 5 degrees from the central optical axis of the system, whereas the angle at which illumination is reflected from the panel in the configuration shown in FIG. 2 is offset 4 degrees from the central optical axis. It is appreciated that the linear motion of the slider provides a continuous selectable displacement of the flat mirror relative to the optical axis, which in turn provides for selectability of a suitable illumination angle along a continuum of possible illumination angles.

FIGS. 3 and 4 represents semi-dark field illumination states each characterized by a different illumination angle that comprises both dark field and bright field components. A continuum of such states is provided by the apparatus of the present invention. In FIGS. 3 and 4, light is output from an optical fiber bundle having a suitable numerical aperture of e.g. 0.6 (angle is +/−)36°. Other light sources having different numerical apertures may be suitable. The propagating beam reflects from an elliptical mirror with a suitable magnification factor of e.g. 1.46.

The Beam Splitter-Mirror Module is set with the Flat Mirror facing the incoming light from the elliptical mirror, the module being arranged to reflect light from the flat mirror towards the panel plane. The slider/beam splitter mirror module is shifted relative to the optical axis to provide a selected angle of illumination. For Semi Dark Field illumination the slider is shifted in a way such that at least some light reflected onto the panel by the flat mirror is subsequently reflected by the panel at an angle such that a least some of the reflected light enters the collecting lens. The extent of the shift is defined by the required semi dark field angle. The light is concentrated onto the panel, and then reflected from it. An objective lens placed along the central optical axis of the system above the panel plane, typically views panel from within an angle of ±3° (6° total), for example.

As shown, the angle at which illumination is reflected from the panel in the configuration shown in FIG. 3 is offset 2 degrees from the central optical axis of the system whereas the angle at which illumination is reflected from the panel in the configuration shown in FIG. 4 is offset 2.5 degrees from the central optical axis. Other suitable angles of offset from the central optical axis may be selected. It is appreciated that translation of the slider results in continuous selectable displacement of the flat mirror relative to the central optical axis, which in turn results in continuous selectable variation of the illumination angle.

Thus in order to achieve dark field illumination, the flat mirror is placed so that light from the panel is reflected at an angle greater than ±3 degrees (in the illustrated embodiment) of offset from the central optical axis. As seen in FIGS. 1 and 2, all of the light reflected from the panel is reflected at an angle greater than ±3 degrees of offset from the central optical axis, but at different degrees of offset. In FIGS. 3 and 4, some of the light reflected from the panel is reflected at an angle greater than ±3 degrees of offset (in the illustrated embodiment) from the central optical axis, and some of the light reflected from the panel is reflected at an angle less than ±3 degrees of offset (in the illustrated embodiment) from the central optical axis, but at different angles of offset. In FIG. 5, substantially all of the light reflected from the panel is reflected at an angle less than ±3 degrees of offset (in the illustrated embodiment) from the central optical axis, such that substantially of the reflected light enters the aperture of the imaging optics.

The apparatus and methods shown and described herein are particularly useful in conjunction with state of the art inspection systems such as the Orbotech SuperVision or In Vision inspection systems, commercially available from Orbotech Systems, Yavne, Israel.

It is appreciated that software components of the present invention, such as a controller for controlling sliding of the slider may, if desired, be implemented in ROM (read only memory) form. Alternatively the software components may, generally, be implemented in hardware, if desired, using conventional techniques.

Features of the present invention which are described in the context of separate embodiments may also be provided in combination in a single embodiment. Conversely, features of the invention which are described for brevity in the context of a single embodiment may be provided separately or in any suitable subcombination.

Although exemplary embodiments of the present invention have been described, it will be understood by those skilled in the art that the present invention should not be limited to the described embodiments, but various changes and modifications can be made within the spirit and the scope of the present invention.

What is claimed is:

1. An inspection method, for use in inspecting an in-fabrication flat panel display with microscopic features, comprising:
   in a first, learning mode:
      sequentially illuminating an object having microscopic features to be inspected with a plurality of illumination angles comprising an angle for dark field illumination of the in-fabrication flat panel display;
      comparing a contrast of the microscopic features under the plurality of illumination angles;
      identifying, from among the plurality of illumination angles, a suitable solid angle of angularly specific illumination, based on the comparison; and
   in a second, inspection mode: inspecting the in-fabrication flat panel display, using said suitable solid angle of angularly specific illumination.

2. A method according to claim 1, wherein the plurality of illumination angles is a continuous range of illumination angles.

3. A method according to claim 1 wherein said plurality of illumination angles further comprises an angle for bright field illumination of the in-fabrication flat panel display.

4. An inspection system for inspecting objects with microscopic features, the system comprising:
   a single light source which provides illumination of an object with microscopic features, the illumination defining a plurality of illumination angles comprising at least an angle of bright field illumination, an angle of dark field illumination, and an angle of semi dark field illumination;
   an object inspector which inspects the object with microscopic features; and
   a controller which controls the object inspector to operate in one of at least two modes including:
      a first, learning, mode in which a suitable solid angle of angularly specific illumination from within said plurality of illumination angles is identified for an individual set of objects with microscopic features by comparing contrast for at least some of the objects in said set when under each of a plurality of illumination angles, and
      a second, inspection, mode in which said individual set of objects is inspected using said solid angle of angularly specific illumination.

5. An inspection system according to claim 4, wherein the plurality of illumination angles is a continuous range of illumination angles.

6. An inspection system according to claim 4, wherein the single light source is a single bundle of optical fibers.

7. An inspection system for inspecting objects with microscopic features, the inspection system comprising:
   an illuminator which provides illumination of an object having microscopic features, the illumination defining a range of a plurality of selectable illumination angles;
   an object inspector which inspects the object with microscopic features under said illumination; and
   a controller which controls the object inspector to operate in one of at least two modes including:
      a first, learning, mode in which a suitable illumination angle from within said range is identified for an individual set of objects having microscopic features by comparing contrast for at least some of the objects in said set when under each of a plurality of illumination angles; and
      a second, inspection, mode in which said individual set of objects is inspected under said suitable illumination angle.

8. An inspection system according to claim 7, wherein the plurality of illumination angles is a continuous range of illumination angles.

9. An inspection system according to claim 7, wherein the illuminator is a single bundle of optical fibers.

10. A system according to claim 7
   wherein said object inspector comprises a collecting lens;
   wherein the object defines an object plane; and
   wherein said illuminator comprises:
      an illumination source;
      a light concentrator;
      an illumination angle selector which is disposed along a light path extending from the illumination source to the object inspector and which, in at least a first selectable position, enables light to propagate toward the object plane;
      a relative motion provider operative to provide motion of the illumination angle selector relative to the illumination source, such that in at least a second selectable position of the illumination angle selector, light selected by the illumination angle selector and incident on the collecting lens is scattered by the object in the object plane.

11. A system according to claim 10 wherein said illumination angle selector comprises a flat mirror.

12. A system according to claim 10 wherein said light concentrator comprises an elliptical mirror.

13. A system according to claim 10, wherein the illumination source is a single bundle of optical fibers.

14. An inspection method, intended for use in inspecting objects with microscopic features, comprising:
   in a first, learning mode:
      sequentially illuminating an object having microscopic features to be inspected with a plurality of illumination angles from a plurality of illumination angles;
      comparing a contrast of the microscopic features under the plurality of illumination angles;
      identifying, from among the plurality of illumination angles, a suitable illumination angle, based on the comparison; and
   in a second, inspection mode: inspecting the microscopic features under the suitable illumination angle.

15. An inspection method according to claim 14, wherein the plurality of possible illumination angles is a continuous range of possible illumination angles.

* * * * *